United States Patent
Wolff

(10) Patent No.: US 7,852,473 B2
(45) Date of Patent: Dec. 14, 2010

(54) APPARATUS FOR MEASURING SPATIALLY RESOLVED THE LUMINESCENCE OF SEMICONDUCTOR SAMPLES

(76) Inventor: Thomas Wolff, Bregstrasse 90, 78120 Furtwangen (DE)

( * ) Notice: Subject to any disclaimer, the term of this patent is extended or adjusted under 35 U.S.C. 154(b) by 201 days.

(21) Appl. No.: 12/272,388

(22) Filed: Nov. 17, 2008

(65) Prior Publication Data
US 2009/0135418 A1    May 28, 2009

(30) Foreign Application Priority Data
Nov. 25, 2007   (DE) .................. 10 2007 056 944

(51) Int. Cl.
*G01N 21/63*   (2006.01)
*G01N 21/01*   (2006.01)
(52) U.S. Cl. ...................... 356/318; 356/244
(58) Field of Classification Search .................. 356/318
See application file for complete search history.

(56) References Cited

U.S. PATENT DOCUMENTS
6,075,592 A    6/2000    Banerjee et al.
2008/0084555 A1*  4/2008    Yoo .......................... 356/73

FOREIGN PATENT DOCUMENTS
EP    0545523 B1    11/1996
EP    0 925 497 B1    2/2003

OTHER PUBLICATIONS

Hanke et al.: "Femtosecond Quantum Optics with Solid State Nanostructures", in: Website of the Chair of Modern Optics and Quantum Electronics, University of Konstanz, Germany, Nov. 2007.
Wettling et al.: "Direct and fast Comparison of Near-Infrared Absorption and Photoluminescence Topography of Semiinsulating GaAs Wafers", in: Appl, Physics, A 40, pp. 191-195, 1986.
Steigmeier et al.: "Light Scattering Topography and Photoluminescence Topography", in: Appl. Phys. A 50, pp. 531-540, 1990.

* cited by examiner

*Primary Examiner*—F. L Evans
(74) *Attorney, Agent, or Firm*—Henry M. Feiereisen; Ursula B. Day

(57) ABSTRACT

An apparatus to measure spatially resolved the luminescence of a semiconductor sample, in particular a semiconductor wafer or any part thereof, includes a rotatable sample holder for the semiconductor sample. This rotatable sample holder is mounted on an xy stage, and a drive mechanism is used to rotate the sample holder rapidly during the measurement. A device excites luminescence light on the semiconductor sample, and an optical device guides a portion of the luminescence light to a detector. The surface of the semiconductor sample is located in the range of a focal point of the optical device. Using a fixation device, it is possible to remove the rotatable sample holder from the xy stage, when required, and to replace it by a cryostat with an optical window and a further semiconductor sample, so that the surface of the further semiconductor sample is essentially located in the focus point of optical device.

21 Claims, 2 Drawing Sheets

APPARATUS FOR MEASURING SPATIALLY RESOLVED THE LUMINESCENCE OF SEMICONDUCTOR SAMPLES

CROSS-REFERENCES TO RELATED APPLICATIONS

This application claims the priority of German Patent Application, Serial No. 10 2007 056 944.2, filed Nov. 25, 2007, pursuant to 35 U.S.C. 119(a)-(d), the content of which is incorporated herein by reference in its entirety as if fully set forth herein.

BACKGROUND OF THE INVENTION

The present invention relates to an apparatus for measuring the luminescence of a semiconductor sample spatially resolved.

To ensure clarity, it is necessary to establish the definition of several important terms and expressions that will be used throughout this disclosure.

The term "spatially resolved" means that the measured luminescence data can be assigned uniquely to singular points of semiconductor surface. If the measurements are based on a Cartesian coordinate system, for example, the luminescence data are sampled together with the x and y coordinates of the measurement points in reference to a point of origin on the semiconductor sample. Alternatively, if the measurements are based on a polar-type coordinate system, for example, the luminescence data is sampled in reference to the angle of a rotatable sample holder and in reference to the linear distance from a point of origin. The point of origin may be, for example, the centre point of the semiconductor sample. With the term "spatially resolved" it is also meant that the semiconductor sample or a part of it is scanned in a two-dimensional way for acquiring the measurement data.

The term "semiconductor sample" relates to a flat sample, which includes completely or in part one or several semiconducting materials, or which is coated at the surface area with at least one semiconducting layer. This sample can be either a flat planar sample without structures, or it can be a sample, which has been processed already by some so-called photolithographic steps, or it can also be a sample with metal contact layers. The surface of the sample can be further coated with translucent layers, for example, layers which are commonly used for passivation in semiconductor technology.

The term "rapidly" or "rapid rotation" relates to rotations in the region of 0.5 to 10 revolutions per second, preferably in the range of 1 to 5 revolutions per second.

To measure the luminescence of semiconductor samples, two measurement apparatus types are known, which hereinafter are referred to as type A and type B.

In a measurement apparatus of type A, the semiconductor sample is driven to a certain point using an xy stage, then stopped, and then a luminescence measurement is performed. For the luminescence measurement, for example, a focused laser beam is used to stimulate luminescence at the sample surface, and the luminescence light thus generated is investigated in a spectrometer. A corresponding apparatus is described in the publication "Publikation des Lehrstuhls für Moderne Optik und Quantenelektronik (LS Leitenstorfer)—Fachbereich Physik—Uni Konstanz" [*Publication of the Chair for Modern Optics and Quantum Electronics (LS Leitenstorfer)—Faculty of Physics—University of Constance*] ("http://www.uni-konstanz.de/quantum-electronics/index3.php?lg=en&sub=4&sub2=1") together with FIG. 2. The laser light passes with its wavelength of 488 nm or 532 nm trough a semi-translucent mirror on a lens, which focuses the laser light on the surface of the sample. This same lens is used to collect the resulting luminescence light. The luminescence light has a smaller energy, i.e. higher wavelength than the stimulating laser light. The semi-translucent mirror is designed such, that it transmits the stimulating laser light, but the longer wavelength luminescence light is reflected, such that the luminescence light is mirrored into the spectrometer for analysis, and the stimulating laser light does not reach the spectrometer. Thus, the spectrometer can be operated at a very high sensitivity, and the stimulating laser light with high intensity will not disturb the measurement of the luminescence light. The laser light hits the semiconductor surface perpendicularly. It is important that the semiconductor sample is located in the focus area of the lens. The focus of the lens can be adjusted by varying its height. The sample and the xy-table are mounted in a low-temperature cryostat. The sample can be cooled down to Helium temperature (4.2K). Typically only relatively small pieces of a semiconductor sample are measured, which fit in the relatively small cryostat. It is not possible, to measure a complete semiconductor with a typical size of 2 to 12 inch diameter. The experimental setup is a laboratory setup and is not intended to be sold as a complete system or apparatus.

A measurement setup according to type A is well known also from Appl. Phys. A 40, p. 191-195 (1986), especially p. 191, right column, last paragraph, to page 192, left column, last paragraph. The measurement here is described as "PLtop" measurement. Here laser light with a wavelength of 514.5 nm is focussed to the surface of a wafer at an angle of about 45 degrees relative to the wafer surface. Stimulated luminescence radiation is collected, passed through 2 filters and then focused into a photomultiplier. It is worth noting here that here—controlled by a computer—a spatially resolved measurement is carried out, but only at room temperature (300K). The article does not specify the measurement time to map a complete semiconductor sample. But experience shows that the mapping of an entire semiconductor wafer with such a setup using an xy stage takes relatively long time.

Another measurement setup in accordance with type A is described in the U.S. Pat. No. 6,075,592. Here, again laser light is focussed vertically on a semiconductor sample. The diameter of the focal point is about 5 μm or 10 μm. The semiconductor sample is placed on a translation stage, so that it can be moved in x, y and z direction. Further there is the possibility to turn the sample initially, i.e. before the actual measurement, if necessary. The excited luminescence light is collected through the same lens and a dichroic coupler is used to separate it from the stimulating laser light, the luminescence light is then sent into an Optical Spectrum Analyzer for analysis. This publication provides no direct reference to the temperature at which is measured. From the details presented it is concluded that the measurements are done at room temperature.

It should be noted, that the turning movement here is meant in the sense of "displacement in turning direction", but not in the sense of "relatively rapid rotation during the measurement"—as it is required for the apparatus described here-in. In other words, the turning of this sample holder serves only for a slow and precise alignment of the semiconductor sample. During the actual measurement the sample holder is not turned. Thus it may be aligned in rotational direction around the z axis; after this alignment the sample holder is not turned further and the actual measurement starts.

European Pat. No. EP 0 925 497 B1 describes an equipment of the type A, which uses a maximum "scan area" of 1 mm×1 mm, which is scanned in the range of minutes. According to its description, this patent is completely restricted to an equipment of the type A. The measurement is performed only at room temperature.

European Pat. No. EP 0 545 523 B1 describes also an equipment of the type A. Here again a fast rotation is not used. The laser used here hits the semiconductor surface under an inclined angle. The excited radiation is collected vertically from the surface and guided into a spectroscope.

In a setup of type B for spatially resolved measurements, the semiconductor sample is fixed on a sample holder which can be rotated horizontally. This sample holder rotates around its vertical axis, while it is shifted in one linear direction of the xy-plane at the same time. Such a design of type B, on which the invention is based as will become apparent later-on, is well known from Applied Physics A50, p. 531-540 (1990), FIG. 1, in conjunction with section 1.1 and 1.2. There the procedure is named PLT procedure (photoluminescence topography). The rotating wafer plate is shifted in this one direction until the entire semiconductor sample has passed a fixed measurement point (focal point) in form of a spiral. At this fixed measurement point the semiconductor sample is hit by a focused laser beam of the wavelength 325.0 nm, 441.6 nm or 632.8 nm. Using a special optical device to focus the laser beam, the laser beam has a radially elongated form of 30 µm*200 µm where it hits the semiconductor surface. Using an optical device which is mounted vertically above the fixed measurement point, the stimulated luminescence light is collected, the laser wavelength is filtered out, and the resulting light is fed into a detector which consists of a photomultiplier. According to this article, an entire semiconductor wafer can be scanned and measured completely.

The apparatus of type B is relatively fast, because the movement of the semiconductor wafer is not stopped during the measurement. But with the apparatus of type B, it is not possible to measure semiconductor samples at low temperatures down to the boiling point of Helium (4.2K) and below. To achieve the low temperatures here, the sample holder with semiconductor would be needed to be in very good thermal contact with liquefied gas. Typically, liquid nitrogen or liquid helium is used. This would require a permanent mechanical connection between the sample holder and a pipe to a liquid gas tank. It is practically impossible, to install this mechanical connection such that the sample holder can rotate. Further the liquid gas tank is so heavy and large, that it would not be practical to rotate it together with the sample holder at a fast speed.

Looking at the currently applied handling in semiconductor laboratories or production facilities, sometimes a device is used to measure relatively large semiconductor samples rapidly at room temperature with a rotatable sample holder, and in addition a device without rotation for low-temperature measurements of relatively small semiconductor samples is used. This approach has the drawback that the complexity is very high. Often such measurements are performed in a clean room, where space is very expensive and limited. In addition, the optical devices used to focus the excitation light, the excitation light sources (lasers), the optical devices to collect the luminescence light, and the spectrometers used as precision detectors are partly very complex, delicate and expensive optical-mechanical devices, which require complex adjustment and calibration steps. If two such devices are used, the complete efforts are typically doubled. Further in many cases it is desirable to compare wide area room temperature measurements with local measurements at low temperature. It is unfavorable to use two different optical systems and/or detectors for such a comparison.

It would therefore be desirable and advantageous to provide an improved measurement apparatus for spatially resolved measurements of luminescence light generated in and emitted from semiconductor samples to obviate prior art shortcomings.

SUMMARY OF THE INVENTION

According to one aspect of the present invention, an apparatus for measuring the luminescence of a semiconductor sample spatially resolved, especially of a semiconductor wafer or any part thereof, includes a rotatable sample holder for holding the semiconductor sample, said sample holder having a drive mechanism for rotating the sample holder rapidly during the measurement, a first device for fixing the semiconductor sample on the sample holder, a first linear stage for driving the rotatable sample holder in x direction, a second device for exciting luminescence light in a surface range of the semiconductor sample, a first detector for measuring the luminescence light, an optical device for guiding the luminescence light of the semiconductor sample to the first detector and defining a height adjustable focal point in an area of the surface of the semiconductor sample, a second linear stage arranged under the rotatable sample holder and forming together with the first linear stage an xy stage on which the sample holder is rotatably mounted, and a fixation device to remove the rotatable sample holder from the xy stage and to put it back on the xy stage or to replace it with a cryostat which is equipped with an optical window and contains a further semiconductor sample having a surface in the range of the focal point.

Hereby a bi-functional device is defined. A special advantage is, that for both kinds of measurements only a single detector is used. Currently preferred is the use of a spectrometer as detector.

For low-temperature measurements the further semiconductor sample, for example, a portion of an entire wafer may be mounted in the above cryostat. To allow good thermal insulation, the cryostat is evacuated well before cooling, and includes an optical window over the horizontally fixed semiconductor sample to allow optical access to the semiconductor surface. The optical window should be not too thick, so that it disturbs the optical measuring as little as possible. Since—after evacuation of the cryostat—the optical window needs to hold appreciable pressure, it should not be too large. This limits the size of the sample which may be scanned in this setup. The evacuation, the subsequent cooling and also the heating after the end of measurement require considerable time. Compared to this time, the time needed for the measurement itself with the scanning of the sample in the x and y direction is not significant for these low temperature measurements.

According to another advantageous feature of the present invention, the cryostat may be designed for operation with liquid helium or liquid nitrogen to cool down the further semiconductor sample to very low temperatures.

According to another advantageous feature of the present invention, the fixation device may include a fixation plate, at which a first carrier, or for replacing the rotatable sample holder by the cryostat, a second carrier can be attached. Suitably, the rotatable sample holder may be mounted on this first carrier using precision ball bearings. It is of advantage, if the fixation plate includes a lower and an upper mounting plate and mounting screws and spring means to allow the adjustment of the inclination of the surface of the rotatable sample holder. Further it is of advantage, if the second carrier includes a lower and an upper plate and mounting screws and spring means to allow the adjustment of the inclination of the cryostat.

According to another advantageous feature of the present invention, the drive mechanism may be constructed as a motor having a high precision rotary encoder, and the first and the second stage may each include a first and second linear encoder, respectively, for measuring the position of these stages in an x direction and in a y direction, respectively, in a high precision manner. Thus if the measurement position of the semiconductor sample on the rotatable sample holder is defined by the rotation of the sample holder and the driving of the first linear stage in x direction, the values of the rotary encoder and the first linear encoder define the exact measurement position. If the measurement position of the further semiconductor sample in the cryostat is defined by the driving of the xy stage which is formed by the first and second linear stage, the values of the first and second linear encoder define the exact measurement position.

The second device for excitation of luminescence light may include at least one laser light source for producing laser light and may include a mirror for directing the laser light into an optical path which leads the laser light to the surface of the semiconductor sample.

The optical device may include at least one lens through which the laser light is guided vertically onto the surface of the semiconductor sample. The lens is further used to collect the luminescence light and to guide this luminescence light to the first detector.

At least one further laser light source may be provided for generating another laser beam and for exciting further luminescence light. This other laser beam hits the surface of the semiconductor sample in an inclined fashion at a further focal point, preferably under 45 degrees, and the optical device should include a further lens for collecting the further luminescence light from the further focal point and for guiding this further luminescence light to the first detector. A second detector may be provided for measuring the overall intensity of the light reflected when the other laser beam hits the surface of the semiconductor sample. The use of drivable mirrors in the optical device is currently preferred for guiding alternatively luminescence light and further luminescence light, respectively, to said first detector or additional detectors.

According to another advantageous feature of the present invention, a video camera and an optical focussing device may be provided, and further an optical element may be provided for placement in the optical path, so that the focussing of the optical device can be monitored using the laser light which is reflected from the surface of the semiconductor sample. Further this video camera can be used for further alignment steps, e.g. to determine the x and y positions of the centre of the rotatable sample holder.

According to another advantageous feature of the present invention, at least a portion of the optical device may be mounted on a lens carrier plate, and the height of this lens carrier plate is adjustable by at least one linear actuator.

It is of particular advantage, if a third detector is provided, and if an optical element is insertable into the space in front of the first detector, such that a portion of the luminescence light is introduced into the third detector, so that the total intensity of the luminescence light can be measured in one fast electrical measurement. Suitably, a high speed transient measuring device may be connected to this third detector. In this case it is advantageous, if the second device for exciting luminescence light is determined for emitting laser light and includes a switching device for switching on the laser light in a switch-on time point and for switching off the laser light in a switch-off time point, wherein the high speed transient measurement is repeatedly started at the switch-off time points of the switching device. The device may further include a computer and the high speed transient measured by the high speed transient measuring device may be used in the computer to determine the lifetime of at least one process in the semiconductor sample, and the lifetime may be captured continuously in dependence of the location of the measurement on the semiconductor sample.

According to another advantageous feature of the present invention, the first detector may be a spectrometer, and a computer may be provided for calculating from the measurement data of the spectrometer a peak wavelength of at least one spectral line, a full width at half maximum (FWHM), an integrated intensity of at least one spectral line, and wherein these values are captured continuously depending on the location of the of the semiconductor sample. This location can be determined by the first linear encoder and the rotary encoder in case of the semiconductor sample mounted on the rotatable sample holder, or by the first linear encoder and the second linear encoder in case of the further semiconductor sample mounted in the cryostat.

According to another advantageous feature of the present invention, the computer may have a monitor for displaying at least one of the values of this peak wavelength, this width at half maximum (FWHM) and this integrated intensity depending on the location of the measurement on the semiconductor sample in a two-dimensional colored diagram or in a three-dimensional diagram. In this way the homogeneity of the semiconductor sample can be checked easily by inspecting such an image. Further this computer can have means for comparing and correlating the images produced from said values. Then the production of semiconductors can be screened by the results of such comparisons or correlations.

BRIEF DESCRIPTION OF THE DRAWING

Other features and advantages of the present invention will be more readily apparent upon reading the following description of currently preferred exemplified embodiments of the invention with reference to the accompanying drawing, in which.

DETAILED DESCRIPTION OF PREFERRED EMBODIMENTS

Figure 1:
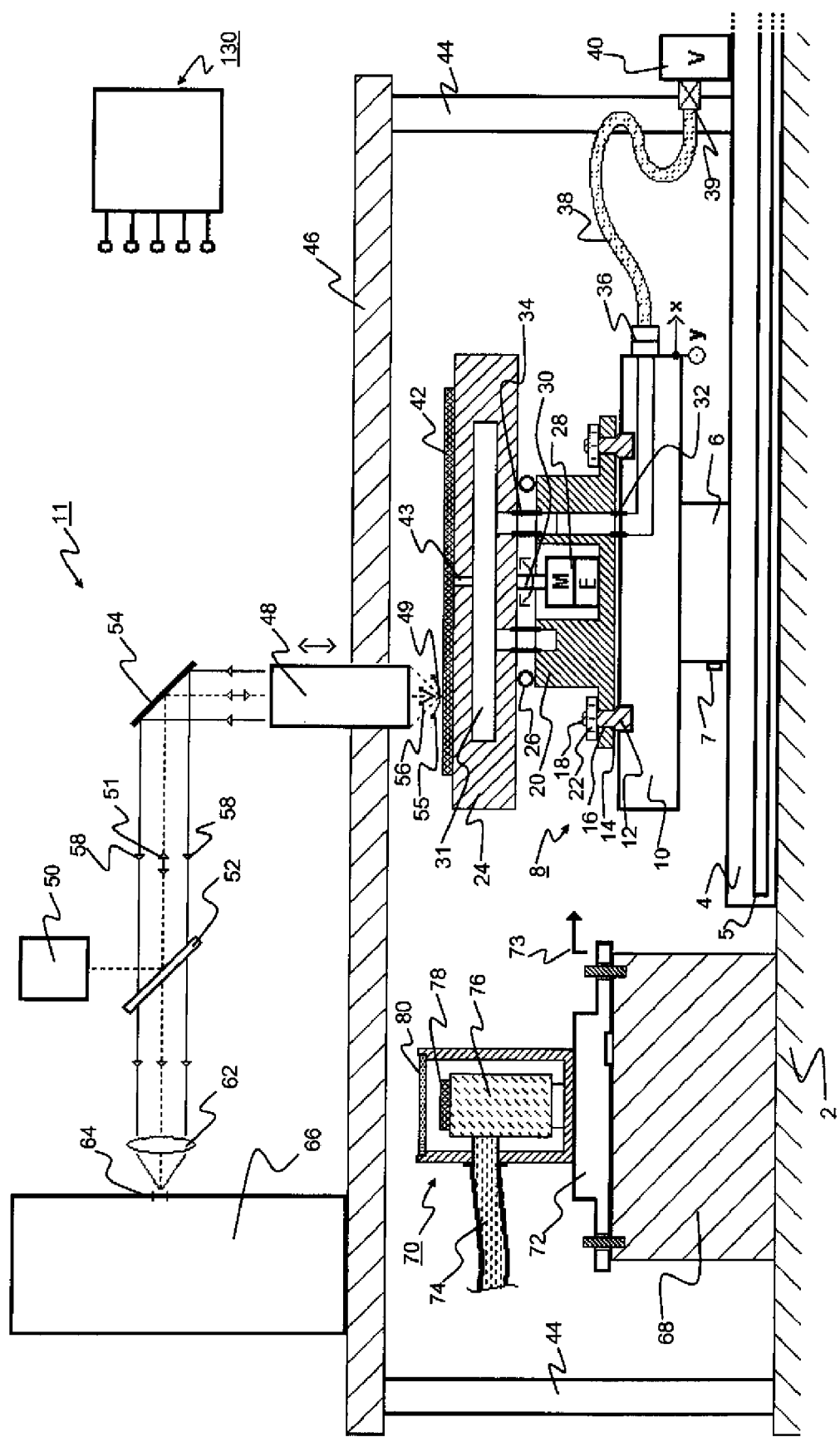
FIG. 1 is a schematic sectional view of an apparatus according to the invention shown.

Throughout all the figures, same or corresponding elements may generally be indicated by same reference numerals. These depicted embodiments are to be understood as illustrative of the invention and not as limiting in any way. It should also be understood that the figures are not necessarily to scale and that the embodiments are sometimes illustrated by graphic symbols, phantom lines, diagrammatic representations and fragmentary views. In certain instances, details which are not necessary for an understanding of the present invention or which render other details difficult to perceive may have been omitted.

Turning now to the drawing, and in particular to FIG. 1, there is shown a schematic sectional view of an apparatus according to the invention, including a solid horizontal base plate 2 on which a first linear stage 4 is mounted, whose carriage can be moved horizontally in x direction. On this carriage the carriage of a second linear stage 6 is mounted, whose guide can be moved in y direction, so that the first stage 4 and the second stage 6 form an xy stage. Such xy stages are driven by two motors (not shown) in the x and y direction, and their positions are recorded using a first linear encoder 5 and a second linear encoder 7, respectively.

On the guide of the second stage 6, a fixation device 8 is mounted. This fixation device 8 includes a fixation plate 10, into which three precision mounting pins 12 are inserted. Over the fixation plate 10, the precision mounting pins 12 diminish at a point 14 into a section 16 with a high precision diameter, which then further is diminished to a thread 18.

A first carrier 20 is placed on the precision mounting pins 12 and fixed with knurled nuts 22. On this first carrier 20, a sample holder 24 is fixed through a precision ball bearing 26, which can be rotated using a centrally mounted motor 28 with rotary encoder E and drive shaft 30.

The sample holder 24 could also be driven using a flexible belt; in this case the motor 28 can be positioned at the side of the first carrier 20. It can also be fixed at the fixation plate 10, and a tensioning device can be used for the belt, which can be easily loosened to take off the first carrier 20 from the fixation plate 10, so that the belt can be removed easily from the drive motor 28. This is not shown here.

A first semiconductor sample 42 can be fixed on the sample holder 24 using vacuum. For this purpose the fixation plate 10, the first carrier 20 and the sample holder 24 each have a feedthrough for vacuum, which lead into a vacuum chamber 31 under the surface of the sample holder 24. Between the fixation plate 10 and the first carrier 20 the vacuum is lead through a detachable vacuum joint 32, and through a rotary vacuum joint between the first carrier 20 and the sample holder 24. A coupling 36 is mounted at the fixation plate 10, to which a vacuum tube 38 is connected, which passes through a vacuum valve 39 to a vacuum pump 40.

On the sample holder 24 the first semiconductor sample 42 can be fixed using the vacuum opening 43. This first semiconductor sample 42 can be, for example, a round wafer with a diameter of 2 to 12 inch, or it can, for example, be a square wafer with an edge length of 10, 15 or 20 cm, or a part of it. The thickness of the semiconductor sample 42 is typically in the range 0.3 to 1 mm, but it can be also very thin down to 0.05 mm or very thick up to 5 mm.

Using posts 44, in parallel to the horizontal base plate 2 an optics base plate 46 is fixed such, that the range of motion of the xy stage 4, 6 is not obstructed. The optics base plate 46 is aligned very carefully parallel to the horizontal base plate 2. In the optics base plate 46 a lens 48 is mounted, whose height can be modified such that the focal point 49 of the lens 48 can be adjusted at the surface of the first semiconductor sample 42. This is indicated by a double arrow.

A laser light source 50 is mounted on the optics base plate 46. A mirror 52, which reflects the laser light 51 selectively, and a totally reflective mirror 54 are mounted such that the parallel light 51 is guided vertically through the lens 48. The mirrors 52, 54 are inclined 45° against the horizontal base plate 2. As the laser light 51 is guided vertically through the lens 48, it is ensured that the optical devices between the lens 48 and the laser light source 50 do not need to be re-adjusted, if the height of the lens 48 is modified to adjust the focal point 49 on the surface of the first semiconductor sample 42. It may be necessary to modify the height of the lens 48, if the thickness of the semiconductor sample 42 varies from one measurement to the next.

Stimulated by the laser light 51, luminescence light 55 is created in the surface range of the semiconductor sample 42. The luminescence light has a longer wavelength than the stimulating laser light 51. A part 56 of the luminescence light, as well as reflected laser light 51 are collected from the lens 48 to form a parallel light beam. This parallel light is reflected at the totally reflective mirror 54 and fed into a parallel optical path 58, which runs parallel to the laser light 51 between the mirrors 52 and 54. The selective mirror 52 is designed such that the luminescence light with longer wavelength is transmitted. Thus this luminescence light is separated from the laser light reflected from the surface of the first semiconductor sample 42. The longer wave luminescence light, which is transmitted by the selectively reflective mirror 52, passes a focussing lens 62 and is focussed on the entrance 64 of a first detector 66, which preferably is a spectrometer.

The motor 28 of the sample holder 24 and the (not shown) two motors of the xy stage 4, 6 are controlled by a computing system 130. This computing system 130 captures the data from the spectrometer 66. For the measurement, the rotating sample holder 24 is driven in the x direction of the first linear stage 4, so that the complete surface of the first semiconductor sample 42 is scanned in form of a spiral. The computing system 130 additionally to the data from the spectrometer 66 captures the angular position of the sample holder 24 using the encoder E of the motor 28, and further it captures the exact position of the xy stage 4, 6 using two linear encoders 5, 7. So for each measurement point the data captured from the spectrometer 66 can be correlated very exactly to a position of the sample holder 24. To define the zero-degree angle position of the sample holder 24 very exactly, a not shown magnet can be mounted in the outer range of the sample holder 24, and a Hall sensor can be mounted at the first carrier 20.

The first linear stage 4 has a large drive range, so that the sample holder 24 can be driven out of the field of the optics base plate 46. In this so-called load position the vacuum chamber 31 is vented using the vacuum valve 39, and the semiconductor sample 42 can be replaced by another semiconductor sample 42 for the following measurement.

In an easily accessible area near the load position, a depositing rack 68 is mounted on the horizontal base plate 2, such that the drive range of the xy stage 4, 6 is not obstructed. For sake of simplicity, FIG. 1 shows the depositing rack 68 positioned below the optics base plate 46, although in reality it is arranged outside the optics base plate 46, so that it can be accessed easily in load position by an operator.

On the depositing rack 68 a low-temperature cryostat 70 is detachably placed, which is mounted on a second carrier 72. The second carrier 72 is designed such that it can be replaced against the first carrier 20 on the fixation plate 10, after the knurled nuts 22 have been loosened. This replacement process is symbolized by a kinked arrow 73. The first carrier 20 and the further carrier 72 have precision fittings, which fit exactly on the precision mounting pins 12 at the sections 16 of high precision diameter. Using the fixation device 8, thus it is possible to replace the carriers 20 and 72 without the need of optical re-alignment of the optical device 11.

The cryostat 70 is connected through a flexible feeder 74 with a not shown control unit to control the circulation of liquid helium, and further with a not shown high-vacuum system. The feeder 74 is positioned in x direction of the first linear stage 4. The flexible feeder 74 has a relatively large length in the range of 1 m or more and slightly hangs through, so that a movement of the cryostat 70 in the direction of the first linear stage 4 does not destroy the flexible feeder 74. The second linear stage 6 has a comparatively small drive range in y-direction of about 5 cm. Due to its length and flexibility the feeder 74 has no problems with the movement of the linear stage 6 in y-direction.

When the cryostat 70 with the second carrier 72 is fixed on the fixation plate 10, and the xy stage 4, 6 has been driven to the load position, the cryostat 70 can be opened at its top. This is not shown here in detail. Inside the cryostat 70 is a further sample holder 76 for another semiconductor sample 78. To attain a good thermal contact and a good fixation, the further semiconductor sample 78 is mounted on the further sample holder 76 using a special paste designed for this purpose. Then the cryostat 70 is closed, it is evacuated through the feeder 74 using the not shown high-vacuum pump system, and it is cooled to ultra low temperature using the not shown Helium flow control system.

Then the cryostat 70 is driven under the lens 48, using the linear stage 4. In its top lid the cryostat 70 has a vacuum tight sealed window 80 made of fused silica, so that it can be evacuated to high-vacuum, but anyway the semiconductor sample 78 can be accessed optically. The window 80 has a diameter of about 20-30 mm and a thickness of about 1-2 mm.

Figure 2:
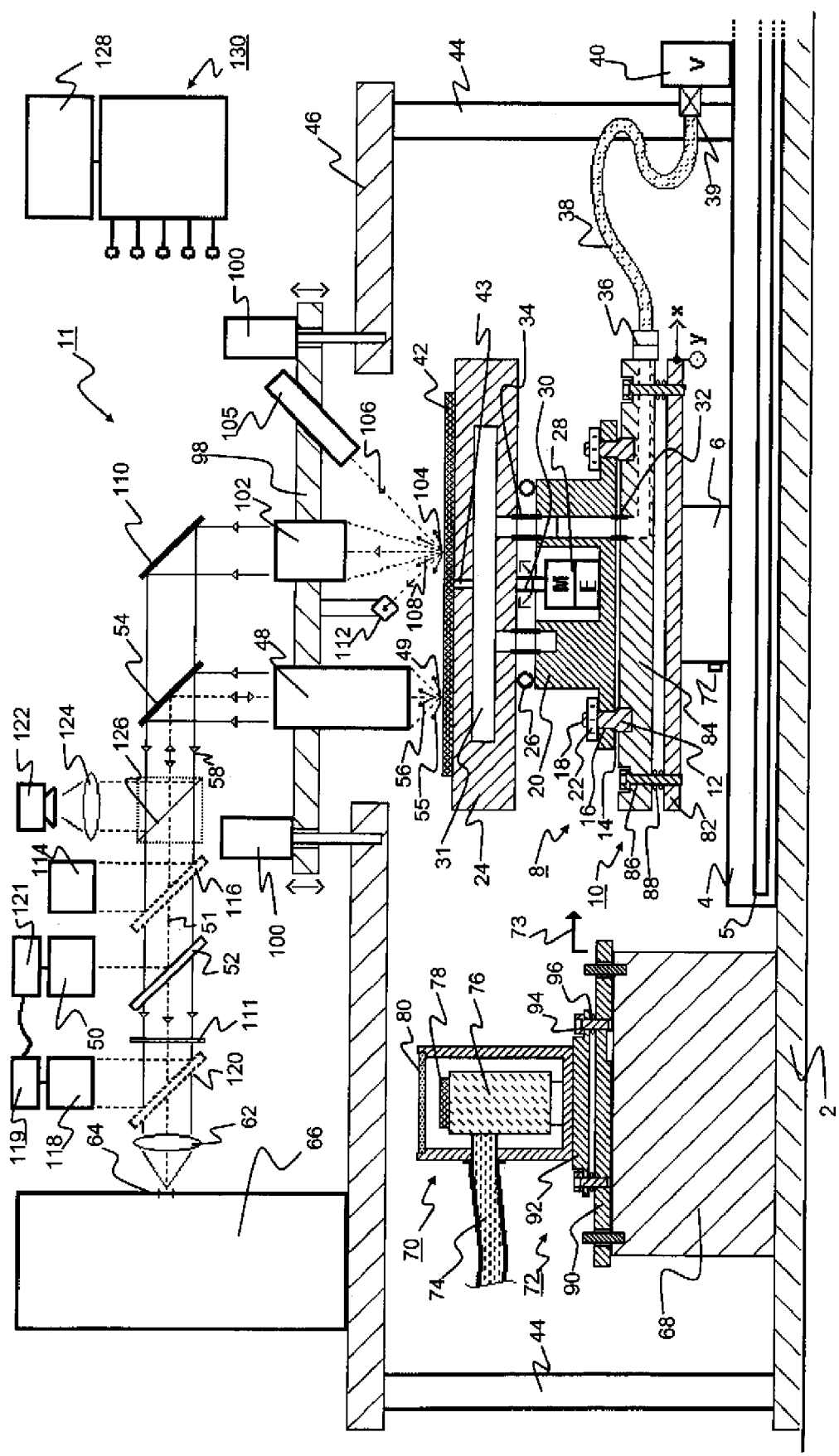
FIG. 2 is a schematic sectional view of the apparatus with further details.

FIG. 2 shows another apparatus containing further details of the fixation plate 10, the carrier 72 and optical devices mounted on the optics base plate 46. Parts corresponding with those in FIG. 1 are denoted by identical reference numerals.

The fixation plate 10 includes a lower mounting plate 82, on which an upper mounting plate 84 is secured using screws 86 and spring washers 88. The first carrier 20 is attached upon the upper mounting plate 84. By adjusting the screws 86, the surface of the rotatable sample holder 24 can be adjusted parallel to the horizontal base plate 2, so that at the focal point 49 the semiconductor sample 42 stays in the same height when the rotatable sample holder 24 is moved in x direction. Further the rotatable sample holder is aligned vertical to rotational axis of the motor 28, so that at the focal point 49 the semiconductor sample 42 keeps in the same height when the rotatable sample holder 24 rotates.

To adjust the tilt of the further semiconductor sample 78 mounted in the cryostat 70, the second carrier 72 comprises a lower plate 90 and an upper plate 92, as well as screws 94 and spring washers 96.

The lens 48 is mounted in a lens carrier plate 98, whose height can be adjusted in the μm range using precise linear actuators 100. This allows to adjust the height of the focal point 49, for example, when semiconductor samples 42, 78 of varying thicknesses are measured. It may also be necessary to vary the height of the focal point 49, if the cryostat 70 together with the further semiconductor sample 78 is used, because the height of the focal point 49 inside the cryostat 70 is modified due to the high-vacuum and the window 80.

In the lens carrier plate 98 a further lens 102 is mounted, whose focal point 104 is displaced in x direction relative to the focal point 49 of the lens 48. Besides the lens 102 a further laser light source 105 is mounted, which uses a non shown optical device to focus its light at an angle of 45° against the surface normal of the semiconductor sample 42 in the area of the focal point 104. The laser light source 105 is shown here so that the laser light 106 forms a spot on the surface of the semiconductor sample 42 which is elongated in x direction. But it can also be mounted such that the laser light 106 forms a light point elongated in y direction (this is not shown in this FIG. 2). This laser light 106 stimulates luminescence light 108 in the surface range of the semiconductor sample 42.

The luminescence light 108 created in the focal point 104 and collected by the further lens 102 is fed into the spectrometer 66 through a mirror 110 and a filter 111. For this purpose the mirrors 52 and 54 are driven out of the parallel optical path 58. The filter in the filter wheel 111 is selected such, that the wavelength of the laser light source 105 is blocked.

Generally, either the laser light source 50 or the further laser light source 105 can be used. For this purpose the mirrors 52 and 54 can be driven. If the further laser light source 105 is used, also the lens 102 is used together with its focal point 104, and the mirrors 52 and 54 are driven out of the optical path 58. If the laser light source 50 is used, preferentially the lens 48 together with its focal point 49 is used, and the mirrors 52 and 54 are driven into the optical path 58. It is also possible to use the laser light source 50 together with the lens 102, then the mirror 52 is driven into the optical path 58, and the mirror 54 is driven out of the optical path 58.

In the following description, first measurements using the lens 48 together with its focal point 49 are described in more detail. Depending on the choice of the carrier 20 or 72 attached to the fixation plate 10, either the semiconductor sample 42 fixed to the sample holder 24, or the further semiconductor sample 78 mounted in the cryostat 70 is measured.

The parallel optical path 58 has a wide length, so that there is enough space to mount four further not shown laser light sources parallel to the laser light source 50 with its selectively reflective mirror 52. Their associated selectively reflective mirrors can be driven into the optical path 58 alternatively. So it is possible, depending on the type of semiconductor samples tested, to use different wavelengths of laser light for stimulation, without the need of replacement or modification of laser light sources. Usual laser wavelengths are, for example, 325 nm, 441 nm, 638 nm. Gas lasers, solid-state lasers or diode lasers can be used. If needed, the frequency of the laser light sources can be increased by known methods of frequency doubling or frequency tripling. It is also possible to compare the results of luminescence measurements at different laser light wavelengths. Typically, to measure a semiconductor sample 42, 78, the laser light wavelength is selected according to the type of the semiconductor sample 42, 78, before the measurement is started.

If the lens 48 is used, the laser light 51 is focussed normally onto the semiconductor sample 42, 78 and the working distance of lens 48 can be very small. The working distance of the lens 102 must be significantly larger, because it must not hinder the laser light 106 which is injected from the side.

Also parallel to the laser light source 50 and the mirror 52, a photodiode 114 can be mounted together with a focussing device, and a beam splitter 116 can be driven into the optical path so that the photodiode 114 can measure the overall intensity of the light reflected at the semiconductor sample 42, thus the luminescence light 56 together with the reflected laser light 51. Spatially resolved, this signal of the photodiode 114 can be captured concurrently with the data of the spectrometer 66.

Furthermore, in the parallel optical path 58 prior to the focusing lens 62, an optical device together with a photodiode 118 can be mounted. This optical device can comprise a mirror 120, which is driven into the optical path so that the photodiode 118 can measure the overall intensity of the luminescence light. The electric signal of this photodiode 118 is captured by a high speed transient measurement device 119 in the nanosecond range. Further the laser light source 50 or another parallel mounted further laser light source can be switched by a switching device 121. The acquisition of the high speed transient measurement device 110 is synchronized to the switch-off time point of the switching device 121. The high speed transient measurement system captures the data of one transient in a very short time of only some milliseconds. This is done repeatedly, while the position of the semiconductor sample 42, 78 is captured by the encoders E, 5, 7. Thus the transients of the luminescence light 56 are captured spatially resolved. From these transients, life times of various processes in the semiconductor material can be determined.

In the following description, measurements are described using the lens 102 with its focal point 104. This lens 102 is used mainly for measurements where the carrier 20 is attached to the fixation plate 10, so that the semiconductor sample 42 is measured on the rotatable sample holder 24. In this case preferentially the further laser light source 105 is used, whose laser light 106 hits the surface of the semiconductor sample 42 in an oblique angle, e.g. of 45°. To measure rotating semiconductor samples 42, it can be important that the light spot of the laser light 106 has an elongated shape at the surface of the semiconductor sample 42. This is easily achieved using this measurement geometry.

Additionally a photodiode 112 can be directed towards the focal point 104 of the lens 102, so that it can measure the intensity of the light which is reflected from the laser light beam 106 at the surface of the semiconductor sample 42. This photodiode 112—as shown here in FIG. 2—can be adjusted such, that it is mounted opposite to the further laser light source 105. Thus it is mounted in the plane, which is formed by the laser light beam 106 and the surface normal of the semiconductor sample 42. But it can also be adjusted such, that it is directed towards the further focal point 104 from the side.

Around the lens 102, further not shown laser light sources can be mounted, which are focussed on the focal point 104 using focussing devices. These laser light sources can be used alternatively to the laser light source 105. The further not shown laser light sources have other wavelengths than the laser light source 105, and they may be used alternatively depending on the type of the semiconductor sample 42. The filter in the filter wheel 111 is then selected such, that the wavelength of the used laser light source is blocked.

Before performing the luminescence measurements, a beam splitter prism 126 can be driven into the parallel optical path 58. This beam splitter 126 feeds the lens 124 focussed into a CCD camera 122 with a part of the laser light in the optical path 58, which has been reflected from the semiconductor sample 42, 78. The image of the camera 122 can be used to check the focussing of the lenses 48 or 102, and to adjust the focussing by varying the height of the lens carrier plate 98. Parallel to the CCD camera 122 and the beam-splitter prism 126, a further not shown white light source together with a further beam splitter can be used to improve the illumination of the semiconductor samples 42, 78, if the intensity of the laser light sources 50, 105 is not sufficient or if the wavelengths of laser light sources are unfavorable for the CCD camera 122.

The entire apparatus shown is controlled by the PC system 130 with a monitor 128. The PC system 130 allows to measure the luminescence spectra captured with the spectrometer 66 spatially resolved, and/or the luminescence transients captured by the high speed transient measurement system 119 and/or the reflected intensities captured using the photodiodes 112, 114. From the spectra further parameters can be calculated automatically, as the peak wavelengths of spectral lines, the full width at half maximum (FWHM) of spectral lines, the integrated intensity of spectral lines. Using the PC system 130, it is possible to display the acquired data in one or more three dimensional images over the semiconductor surface, or to create two dimensional color images of the semiconductor surface using a configurable color scale. These images can be shown on the monitor 128 and also stored by the computer system 130. These images or superimposition of these images can be compared to reference images, and depending on such comparisons a wafer can be qualified as good or bad. The statistical data of such measurement values can be reported in statistical control charts to allow continuous automated monitoring of a semiconductor production.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed as new and desired to be protected by Letters Patent is set forth in the appended claims and includes equivalents of the elements recited therein:

What is claimed is:

1. Apparatus for the spatially resolved measurement of a luminescence of a semiconductor sample, in particular of a semiconductor wafer or any part thereof, said apparatus comprising:
   a rotatable sample holder for holding a semiconductor sample, said sample holder having a drive mechanism for rotating the sample holder rapidly during the measurement;
   a first device for fixing the semiconductor sample on the sample holder;
   a first linear stage for driving the rotatable sample holder in x direction;
   a second device for exciting luminescence light in a surface area of the semiconductor sample;
   a first detector for measuring the luminescence light;
   an optical device for guiding the luminescence light of the semiconductor sample to the first detector and defining a height adjustable focal point in an area of the surface of the semiconductor sample;
   a second linear stage arranged under the rotatable sample holder and forming together with the first linear stage an xy stage on which the sample holder is rotatably mounted; and
   a fixation device to remove the rotatable sample holder from the xy stage and to put it back on the xy stage or to replace it with a cryostat which is equipped with an optical window and contains a further semiconductor sample having a surface in the range of the focal point.

2. The apparatus of claim 1, wherein the cryostat is designed for operation with liquid helium (He) or liquid nitrogen ($N_2$) to cool down the further semiconductor sample.

3. The apparatus of claim 1, wherein the fixation device comprises a fixation plate for attachment of a first carrier, or for attachment of a second carrier, when the rotatable sample holder is replaced by the cryostat.

4. The apparatus of claim 3, further comprising a precision ball bearing to mount the rotatable sample holder on the first carrier.

5. The apparatus of claim 3, wherein the fixation plate comprises a lower mounting plate, an upper mounting plate which is connected to the lower mounting plate by mounting screws, and spring means interposed between the lower and upper mounting plates to allow adjustment of an inclination of the rotatable sample holder.

6. The apparatus of claim 1, wherein the drive mechanism is a motor having a high precision rotary encoder, the first stage comprising a first linear encoder and the second stage comprising a second linear encoder for measuring a position of the first and second stages in x direction and in y direction, respectively.

7. The apparatus of claim 3, wherein the second carrier comprises a lower plate, an upper plate which is connected to the lower plate by mounting screws, and spring means to allow adjustment of an inclination of the cryostat.

8. The apparatus of claim 1, wherein the second device comprises at least one laser light source for producing laser light and a mirror for directing the laser light into an optical path which leads the laser light to the surface of the semiconductor sample in the focal point.

9. The apparatus of claim 8, wherein the optical device comprises at least one lens through which laser light is guided vertically onto the surface of the semiconductor sample and which collects the luminescence light to guide the luminescence light to the first detector.

10. The apparatus of claim 1, further comprising at least one laser light source for generating a laser beam and exciting luminescence light, wherein the laser beam hits the surface of the semiconductor sample obliquely in a further focal point, said optical device including a lens for collecting the luminescence light from the further focal point and guiding the luminescence light to the first detector.

11. The apparatus of claim 10, further comprising a second detector for measuring an overall intensity of light reflected when the laser beam hits the surface of the semiconductor sample.

12. The apparatus of claim 10, wherein the optical device includes drivable mirrors for alternatingly guiding the luminescence light excited by the second device and the luminescence light excited by the laser light source to the first detector.

13. The apparatus of claim 8, further comprising an optical element insertable in the optical path for directing the laser beam to a video camera and an optical focussing device to monitor a focussing of the optical device as the laser beam is reflected from the surface of the semiconductor sample.

14. The apparatus of claim 1, further comprising a lens carrier plate for attachment of at least a portion of the optical device, and at least one linear actuator for height adjustment of the lens carrier plate.

15. The apparatus of claim 1, further comprising a third detector, and an optical element insertable into a space in front of the first detector, such that a portion of the luminescence light is introduced into the third detector.

16. The apparatus of claim 15, further comprising a high speed transient measuring device connected to the third detector.

17. The apparatus of the claim 16, wherein the second device is determined for emitting laser light and comprises a switching device for switching on the laser light in a switch-on time point and for switching off the laser light in a switch-off time point, and wherein the high speed transient measurement is repeatedly started at the switch-off time points of the switching device.

18. The apparatus of claim 6, wherein the first detector is a spectrometer, further comprising a computer for calculating in response to measurement data of the spectrometer, parameters selected from the group consisting of a peak wavelength of at least one spectral line, a full width at half maximum (FWHM), and an integrated intensity of at least one spectral line, and wherein the measurement data is captured continuously depending on a location of the semiconductor sample determined by the precision rotary encoder and the first and second linear encoders.

19. The apparatus of claim 17, further comprising a computer operatively connected to the high speed transient measuring device to determine a lifetime of at least one process in the semiconductor sample, with the lifetime captured continuously in dependence of a location of the measurement on the semiconductor sample.

20. The apparatus of claim 18, wherein the computer has a monitor for displaying at least one of the parameters in a two-dimensional colored diagram or in a three-dimensional diagram.

21. The apparatus of claim 18, wherein the computer is constructed to compare and correlate images produced from the parameters.

* * * * *